United States Patent [19]
Viole et al.

[11] Patent Number: 5,319,116

[45] Date of Patent: Jun. 7, 1994

[54] LECITHIN FRACTIONS AND DILUTIONS, METHODS FOR THEIR PREPARATION AND PHARMACOLOGICAL USES THEREOF

[76] Inventors: Gary Viole, 734 Howard Rd., Ridgewood, N.J. 07450; Majid Ali, 8 Alcott Ct., Teaneck, N.J. 07666

[21] Appl. No.: 834,644

[22] Filed: Feb. 12, 1992

[51] Int. Cl.[5] .............................................. C07F 9/02
[52] U.S. Cl. .......................................... 554/83; 554/80
[58] Field of Search ...................... 554/10, 93, 83, 30; 514/78

[56] References Cited

U.S. PATENT DOCUMENTS

| | | | |
|---|---|---|---|
| 4,093,540 | 6/1978 | SenGupta | 554/80 |
| 4,415,733 | 11/1983 | Tayot | 536/53 |
| 4,416,872 | 11/1983 | Alving et al. | 536/53 |
| 4,474,773 | 10/1984 | Shinitzky et al. | 514/78 |
| 4,496,489 | 1/1985 | Sen Gupta | 554/83 |
| 4,563,354 | 1/1986 | Chang et al. | 425/195.1 |
| 4,694,069 | 9/1987 | Dingerdissen et al. | 530/317 |
| 4,814,111 | 3/1989 | Kearns et al. | 554/83 |
| 4,829,009 | 5/1989 | Graves | 436/518 |
| 4,849,137 | 7/1989 | Kobayashi | 554/83 |
| 4,871,540 | 10/1989 | Kojima et al. | 424/195.1 |
| 4,876,199 | 10/1989 | Hakomori | 530/387.5 |

FOREIGN PATENT DOCUMENTS

| | | |
|---|---|---|
| 0213724 | 3/1987 | European Pat. Off. . |
| 0214055 | 3/1987 | European Pat. Off. . |
| 0239729 | 10/1987 | European Pat. Off. . |
| 55-54861 | 1/1980 | Japan . |
| 55-50859 | 4/1980 | Japan . |
| 62-246525 | 10/1987 | Japan . |
| 2004741 | 4/1979 | United Kingdom . |

Primary Examiner—Thurman K. Page
Attorney, Agent, or Firm—Shea & Gould

[57] ABSTRACT

Disclosed are compositions comprising neutral, negatively and positively charged glycolipids phospholipids derived from lecithin, particularly lecithin fractions, and dilutions of lecithin or lecithin fractions. Also disclosed are methods for the preparation of such compositions, dosage units comprising these compositions, and methods of treatment of warm-blooded animals, preferably humans, with such compositions. These compositions are individually, collectively and selectively useful in the treatment of bacterial, viral, and skin infections and diseases.

4 Claims, 8 Drawing Sheets

LECITHIN FRACTIONS AND DILUTIONS, METHODS FOR THEIR PREPARATION AND PHARMACOLOGICAL USES THEREOF

FIELD OF THE INVENTION

This invention relates to compositions comprising neutral, negatively, and positively charged glycolipids and phospholipids derived from lecithin, particularly lecithin fractions, and dilutions of lecithin or lecithin fractions. This invention also relates to methods for the preparation of such compositions, dosage units comprising these compositions, and methods of treatment of warm-blooded animals, preferably humans, with such compositions. These compositions are individually, collectively and selectively useful in the treatment of bacterial, viral, and skin infections and diseases.

All such glycolipids, fractions, dilutions, dosage units, processes and methods of treatment are included within the present invention.

BACKGROUND OF THE INVENTION

Novel processes have been discovered for the preparation of novel lecithin derived glycolipids and phospholipids. Those lecithin derived glycolipids and phospholipids and dilutions thereof, as well as lecithin dilutions, and the dosage unit forms which have been discovered are useful in the treatment of a wide range of diseases. These lecithin fractions and dilutions have superior purity and pharmacological capabilities. Methods of treatment of warm-blooded animals using either or both the products of these methods and/or specific lecithin dilutions have also been discovered.

Shinitzky et al., U.S. Pat. No. 4,474,773, disclose lipid extracts obtained from egg yolk or soybean which are said to be useful for treating various diseases and physiological conditions as well as a process for the fractionation of lipids. The fractionation is effected by dissolving a lipid extract in a suitable solvent, evaporating the solvent to almost complete dryness, precipitating a fraction of the dissolved lipids by the addition of an organic solvent, and recovering the desired fraction from the supernatant. Three preferred methods of fractionation are exemplified. The first method involves dissolving the lipid extract in chloroform, evaporating to near dryness, and precipitating by the addition of acetone. The supernatant is removed and is evaporated to near dryness, leaving a fraction of about 5 weight percent of the untreated extract as the active lipid. The second method mixes a natural lipid source with acetone to remove excess undesired lipids. The precipitate is treated again with acetone, and the supernatant is collected and is evaporated to complete dryness, leaving the desired fraction which is about 10 to 15 weight percent of the initial quantity of the lipid source. In the third method, a natural lipid source is mixed with acetone to remove excess undesired lipid. The precipitate is treated again with acetone, and the supernatant is collected and is cooled below 0° C. at which time the active lipid (about 10 to 15 weight percent of the initial quantity of the lipid source) is precipitated and is collected.

Chang et al., U.S. Pat. No. 4,563,354, disclose alcohol-soluble fractions of vegetable lecithin which are suitable for use as emulsifiers for oil-in-water emulsions. These fractions are well-tolerated when used for parenteral nutrition. The Chang et al. extraction process includes a preliminary purification of the lecithin which involves dissolving the lecithin in a solvent such as hexane, and precipitating the lecithin through the use of acetone. The precipitated lecithin is then extracted with an alcohol at a temperature ranging from −20° C. to slightly elevated temperatures in order to extract the alcohol-soluble portion of the lecithin. The extraction may be repeated multiple times. The filtrate(s) from the alcohol extraction step(s) are combined and are chilled to about −20° C. for about 24 hours to produce a precipitate. Any solids which separate are removed by filtration and are discarded. The resulting filtrate is freed of solvent under vacuum and is again dissolved in alcohol. The resulting solution is chilled, again utilizing a temperature of about −20° C. for about 24 hours. The precipitate is then removed by filtration and is discarded. The resulting filtrate again is treated under vacuum to remove solvent, and the residue is precipitated from acetone to yield the alcohol-soluble soybean phospholipid fraction.

U.K. Patent Publication No. 2,004,741 illustrates a composition which is said to be useful in treating baldness, burns and various viral complaints and which contains cholesterol, an unsaturated fatty acid, and a phosphoamino-lipid. The phosphoamino-lipid utilized in the composition may be egg lecithin or vegetable lecithin.

Japanese Patent Publication No. 55/50859 discloses a method for refining lecithin from, for example, soybean oil, by adding propylene glycol to extract the oil and using an aqueous organic acid to coagulate the lecithin. The extraction is practiced at below 80°C.

Japanese Patent Publication No. 55/054861 also deals with a method for treating crude lecithin-containing oil by adding propylene glycol, mixing to extract the lecithin, adding a group II metal chloride, mixing, and separating the coagulated lecithin.

Japanese Patent Publication No. 62/246525 relates to a pharmacological lecithin mixture which is prepared by suspending phosphatidyl choline, phospholipid mixture and neutral lipid in an alcohol solvent, filtering, and removing the solvent. This lecithin mixture contains at least 75 weight percent phosphatidyl choline, 5 to 13 weight percent of an ethanol amine and phosphatidic acid-containing phospholipid mixture, and 0 to 20 weight percent of neutral lipid. The lecithin mixture is derived from animal or vegetable sources such as seeds, fruit, egg yolk, soybean, and the like and is useful as a medicine for arteriosclerosis, hyperlipemia, liver diseases, heart attack, and the like.

European Patent Application No. 0,213,724 relates to a lipid mixture for membrane fluidization consisting of about 7 parts by weight of neutral lipids and about 3 parts by weight of phospholipids. The phospholipids consist of phosphatidyl choline, phosphatidyl ethanol amine, and neutral lipids consisting essentially of glycerides.

European Patent Application No. 0,214,055 discloses an artificial surfactant which is a mixture of dipalmitoyl phosphatidyl choline, distearoyl phosphatidyl choline and soybean lecithin. Soybean lecithin is a well-known adjuvant for intravenous preparations, and the soybean lecithin utilized in EPO '055 has a molecular weight of about 780.

European Patent Application No. 0,239,729 relates to polyprenyl alcohol-containing injections comprising certain polyprenyl alcohols and lecithin as an essential ingredient. The addition of a lecithin increases activity of the polyprenyl alcohol in in vivo applications.

Tayot, U.S. Pat. No. 4,415,733, discloses ganglioside derivatives which are products of partial deacylation of gangliosides. Free amino groups are demonstrated by a positive reaction in a ninhydrin test, are mobile in chromatograph on a thin silica gel layer in the chloroform-butanol-water system (60:32:7), and exhibit specific affinity properties of the gangliosides from which they are derived. The derivatives are able to couple to solid supports by amino groups that have appeared during partial deacylation without loss of specific affinity properties. Tayot also relates to a process of preparing these activated ganglioside derivatives while retaining their biological properties. The activated gangliosides are treated with an aqueous base solution at a temperature between 0° and 120° C. The lower temperatures require more basic medium. The reaction time for partial deacylation varies from 30 minutes to 24 hours. The transformation is reflected by the appearance of at least an $-NH_2$ function resulting from partial hydrolysis of the N-acetyl or N-acyl function in sufficient number to allow fixing by the known methods, but limited enough to maintain the biological properties of the gangliosides.

Alving et al., U.S. Pat. No. 4,416,872, disclose a method for the prophylaxis and the chemotherapeutic treatment of malaria with antimalarial compositions comprising either a glycolipid alone, a glycoprotein encapsulated within a liposome, or an 8-aminquinoline drug and a glycoconjugate contained within a liposome. The liposome (exclusive of the glycoconjugate constituent) may contain a combination of (1) a phospholipid and cholesterol or (2) a phospholipid, cholesterol and a negatively or positively charged (lipophilic) amphipathic compound. Glycolipids having a terminal glucose or galactose moiety are said to be effective when incorporated within the liposomes. The amphipathic component, by way of example, can be diacetyl phosphate or stearylamine to impart charge to the liposomes. Glycolipids having a terminal glucose or galactose moiety are said to be effective when incorporated within the liposomes.

Dingerdissen et al., U.S. Patent No. 4,694,069, disclose glycopeptide AAD-609 antibiotics which are structurally and biologically related to the AAD-216 antibiotics. The AAD-609 antibiotic varies from AAD-216 antibiotic in that the sugar moiety within the glycolipid radical is glucosamine rather than aminoglucuronic acid. Pharmaceutical compositions containing at least one of the AAD-609 factors and a pharmaceutically acceptable carrier are discussed as well. The compositions may additionally contain other active antibacterial agents.

Graves, U.S. Pat. No. 4,829,009, discloses matrix layers suitable for solid phase immunoassays useful in eliminating false positives. Graves provides a means for verification of the effectiveness of such matrix layers and for maximizing their effectiveness, as well as for quantitation of background noise. Generally, the noise reduction component will provide an anionic barrier and therefore will be a negatively charged material, preferably a macromolecule. Any negatively charged (at neutral pH) protein, glycoprotein, polyamino acid or other natural or synthetic macromolecule could be used as a noise reduction component. Graves also includes a method of designing a protocol to determine simultaneously the values of three parameters—sensitivity ratio, signal to noise ratio, and noise balance ratio—which collectively influence the matrix index.

Kojima et al., U.S. Pat. No. 4,871,540, disclose a process for producing a biologically active substance of plant origin, having interferon-inducing activity. The substance is said to be useful for preventing and treating, for example, aesthema, rhintitis, B-type hepatitis, AIDS and other allergic diseases and immunological insufficiencies. The active substance is said to be capable of inhibiting the formation of IgE antibodies, promoting the formation of IgG and IgM antibodies and having interferon inducing activity, polyclonal B lymphocyte activating activity, mitogenic activity, adjuvant activity and anti-tumor activity.

Hakomori, U.S. Pat. No. 4,876,199, relates to hybridoma cell lines that produce monoclonal antibodies which differentially recognize glycolipids with mono-, di- and trifucosylated type 2 chain structures. These monoclonal antibodies are said to be useful for detecting specific types of tumor cells in the diagnosis and the treatment of human cancer.

Stolze and Khaden, *Institute of Virology*, "Apparent Lack of Neutralizing Antibodies in Aleutran Diseases Is Due to Masking of Antigenic Sites by Phospholipids", Academic Press, Inc., 1987, discuss neutralization of Aleutian disease virus by phospholipids.

Nakashima et al. "Inhibitory Effect of Glycosides Like Saponin From Soybean on the Infectivity of HIV In Vitro, AIDS Vol. 3, p. 655-658 (1989), describe soybean saponins isolated from the soybean seeds which were investigated for their antiviral activity on HIV in vitro, using an HTLV-1-carring cell line, NT-4. One of the saponins (identified as saponin B1) completely inhibited HIV-induced cytopathic effects and virus-specific antigen expression six (6) days after infection at concentrations greater than 0.5 milligrams per milliliter. Another saponin (identified as saponin B2) also inhibited HIV infection, although less potently. Both saponins are reported to have had no directed effect on the reverse transcriptase activity of HIV. Saponin B1 was reported to have also inhibited HIV-induced cell fusion in the MOLT-4 cell system.

The present applicants believe that the activity described by Nakashima et al. is limited to in vitro activity. The present applicants have found that the in vivo activity of the presently described lecithin fractions and dilutions is dependent upon at least some phospholipid content residing in the lecithin fractions and/or dilutions.

The present applicants have found that as the content of phospholipid with its complexing agents is reduced, the in vivo activity is also reduced.

SUMMARY OF THE INVENTION

According to the present invention, there is provided a method (herein "Procedure I") for producing a lecithin derived fraction, said method comprising:

(a) mixing lecithin or a lecithin source and an aqueous polar organic solvent solution;

(b) heating the mixture to yield a first liquor fraction and a first insoluble fraction;

(c) mixing an aqueous polar organic solvent solution which may be the same as or different than the aqueous polar organic solvent solution of step (a) with the first insoluble fraction;

(d) heating the mixture of step (c) to yield a second liquor fraction and a second insoluble fraction;

(e) combining the first liquor fraction with the second liquor fraction to yield a combined liquor fraction;

(f) heating the combined liquor fraction to yield a third liquor fraction and a third insoluble fraction; optionally performing the following step (g), or proceeding directly to step (h);

(g) cooling and reheating the third liquor fraction to yield a supplemental third liquor fraction and a supplemental third insoluble fraction;

(h) removing any residual aqueous polar organic solvent solution from the third liquor fraction (or the optional supplemental third liquor fraction) to yield residual solids;

(i) mixing the residual solids with polar organic solvent for a period of time sufficient to leach out any remaining soluble materials from the residual solids to produce remaining residual solids; and optionally (j) isolating the remaining residual solids.

In a preferred embodiment, this Procedure I method also includes either a step (k-1) in which the remaining residual solids are separated into a white powder component and a yellow crystalline component, or a step (k-2) wherein the remaining residual solids are diluted with a trihydric alcohol solvent.

The present invention also includes: the composition produced by the process of steps (a-j) above which is designated herein as Component C; the white powdery composition separated in step (k-1) above which is designated herein as Component D; the yellow crystalline composition separated in step (k-1) above which is designated herein as Component G; and the diluted Components C, D and/or G prepared in step (k-2).

Additionally, the present invention includes methods of treatment of viral infections by the selective, collective or sequential administration of independent anti-viral effective amounts of Component C, Component D, Component G, or dilutions of Components C, D and/or G.

Further, dosage units comprising independent anti-viral effective amounts of the compositions above, alone or in combination of two or more, are contemplated as well in the present invention.

Alternatively, a second method (herein the "Procedure II") for the production of a lecithin derived fraction is provided, said method comprising:

(a) mixing lecithin or a lecithin source and an aqueous polar organic solvent solution;

(b) heating the mixture to yield a first liquor fraction and a first insoluble fraction;

(c) mixing an aqueous polar organic solvent solution which may the same as or different than the aqueous polar organic solvent solution of step (a) with the first insoluble fraction;

(d) heating the mixture of step (c) to yield a second liquor fraction and a second insoluble fraction;

(e) combining the first liquor fraction with the second liquor fraction to yield a combined liquor fraction;

(f) heating said combined liquor fraction to yield a third liquor fraction and a third insoluble fraction; optionally (g) cooling and reheating the third liquor fraction to yield a supplemental third liquor fraction and a supplemental third insoluble fraction;

(h)(1) removing any residual aqueous polar organic solvent from the third liquor fraction or the optional third supplemental liquor fraction to yield residual solids, and (2) heating repeatedly the residual solids in a polar organic solvent until no color is imparted to the polar organic solvent to yield a solvent liquor fraction and to produce remaining residual solids; optionally (i) isolating the remaining residual solids.

In a preferred embodiment, this Procedure II method also includes either a step (j-1) in which the remaining residual solids are separated into a white powder component and a yellow crystalline component, or a step (j-2) in which the remaining residual solids, or combinations, are diluted with a trihydric alcohol solvent.

The present invention also includes: the composition produced by steps (a-i) above which again is Component C; the white powdery composition separated in step (j-1) above which again is Component D; the yellow crystalline composition separated in step (j-1) above which again is Component G; and the diluted Component C prepared in step (j-2).

These compositions may again be incorporated in methods for the treatment of viral infections by the selective, collective, or sequential administration of independent anti-viral effective amounts, and in dosage units comprising anti-viral effective amounts, of the compositions above.

The lecithin derived fractions of the insoluble fractions from Procedure I and/or Procedure II, which are designated herein as Component S-2, can be also prepared by a method (herein "Procedure III"), said method comprising:

(a) mixing lecithin or a lecithin source and an aqueous polar organic solvent solution;

(b) heating the mixture to yield a first liquor fraction and a first insoluble fraction;

(c) mixing an aqueous polar organic solvent solution which may the same as or different than the aqueous polar organic solvent solution of step (a) with the first insoluble fraction;

(d) heating the mixture of step (c) to yield a second liquor fraction and a second insoluble fraction;

(e) combining the first liquor fraction with the second liquor fraction to yield a combined liquor fraction;

(f) cooling and heating the combined liquor fraction to yield a third liquor fraction and a third insoluble fraction; (repeat, optionally, step (f) or proceed directly to step (g))

(g) combining the third insoluble fraction with the second insoluble fraction to yield a total insoluble fraction.

A preferred embodiment of Procedure III includes a step (h) in which the third insoluble fraction or the optional total insoluble fraction is diluted with a trihydric alcohol solvent.

Also contemplated are the compositions produced by steps (a-g). These compositions are probacterial and probiotic and can be used in sewage treatments, such as for providing a favorable environment for growth of sewage-treatment bacteria, or can be used in agricultural environments, such as for providing a favorable environment for growth of seeded nitrogenyielding bacteria.

Additionally, according to the present invention, there is provided a method (herein "Procedure IV") for producing lecithin derived fraction, said method comprising:

(a) mixing lecithin or a lecithin source in a polar organic solvent to provide a mixture;

(b) curing the mixture to yield a liquor fraction and an insoluble fraction;

(c) cooling the liquor fraction to provide a precipitant fraction and a polar organic solvent-based supernatant liquor fraction;

(d) reducing the amount of polar organic solvent in the supernatant fraction;

(e) cooling the reduced supernatant liquor fraction to provide three fractions comprising a lower solid fraction, an intermediate liquor fraction, and an upper liquor fraction; and optionally (f) reducing the amount of polar organic solvent in the upper liquor fraction.

In a preferred embodiment, Procedure IV includes the further step:

(g) dissolving or diluting the reduced supernatant upper liquor fraction in a trihydric alcohol solvent.

Also contemplated are the compositions produced by steps (a-f) and/or (a-g) of Procedure IV, herein referred to as Component 6 and/or dilutions of Component 6. Component 6 can also be combined with Component C, for example.

Preferred embodiments include a method of treating bacterial infection in a warm-blooded animal comprising administering an anti-bacterial effective amount of Component 6, a dilution of Component 6, a dosage unit form comprising an antibacterial effective amount of Component 6, and/or a dilution of Component 6. The insoluble fraction from step (b) is Component 2 which exhibits anti-viral activity when in, inter alia, glycerin solutions.

According to still another embodiment of the present invention, there is provided a method (herein "Procedure V") for producing a lecithin derived fraction, said method comprising:

(a) mixing lecithin or a lecithin source in a heated aqueous polar organic solvent solution to yield a lower insoluble fraction and an upper liquor fraction;

(b) separating the two fractions;

(c) cooling the liquor fraction and re-heating to produce a second liquor fraction and a second insoluble fraction.

(d) removing the aqueous polar organic solvent from the second liquor fraction to yield the residual solids;

Also contemplated is an additional step to Procedure V:

(e) adding an alcohol solvent, preferably a trihydric alcohol solvent.

Further contemplated by the present invention are compositions produced by the processes of steps (a-d) and of steps (a-e) of Procedure V, herein referred to as Component S-6 and/or dilutions of Component S-6.

Additionally, the present invention provides for methods for the treatment of bacterial and viral infections in warm-blooded animals comprising the selective, collective or sequential administration of independent anti-bacterial- and/or anti-viral-effective amounts of Component S-6, and/or dilutions of Component S-6.

Dosage units comprising anti-bacterial-effective amounts and anti-viral-effective amounts of Component S-6, and/or dilutions of Component S-6 are provided as well.

According to yet another embodiment of the present invention, there is provided a method (herein "Procedure VI") for producing lecithin derived fraction, said method comprising:

(a) mixing lecithin or a lecithin source in an aqueous polar organic solvent solution;

(b) heating the mixture for a time sufficient to yield a yellow liquor above an amber lower layer;

(c) agitating the yellow liquor and amber lower layer while maintaining the heated temperature to obtain an agitated mixture;

(d) ceasing the agitation and allowing the agitated mixture to separate, while maintaining the temperature, to form an opaque yellow liquor above a bottom layer; and, (e) separating and optionally cooling the opaque yellow liquor to form a solidified portion and a liquor portion.

Further contemplated by the present invention are compositions produced by the processes of steps (a-d), with the top layer thereof herein referred to as Component SH-6 and the bottom layer thereof herein referred to as Component SH-2, as well as compositions produced by the process of steps (a-e), with the solidified portion after cooling herein referred to as Component SH-8, and with the liquor portion remaining after cooling herein referred to as Component SH-7. Dosage units and methods of treatments employing the above compositions are also contemplated.

Still further, lecithin dilutions with an alcohol solvent, preferably a trihydric alcohol solvent, are contemplated herein. Particularly contemplated are positively charged glycolipids and dilutions thereof. These compositions may be used for the treatment of skin, bacterial, and viral infections by the administration of epidermal-treating, anti-bacterial- or anti-viral-effective amounts thereof. Dosage units of these amounts are also provided.

DETAILED DESCRIPTION OF THE INVENTION

Figure 1:
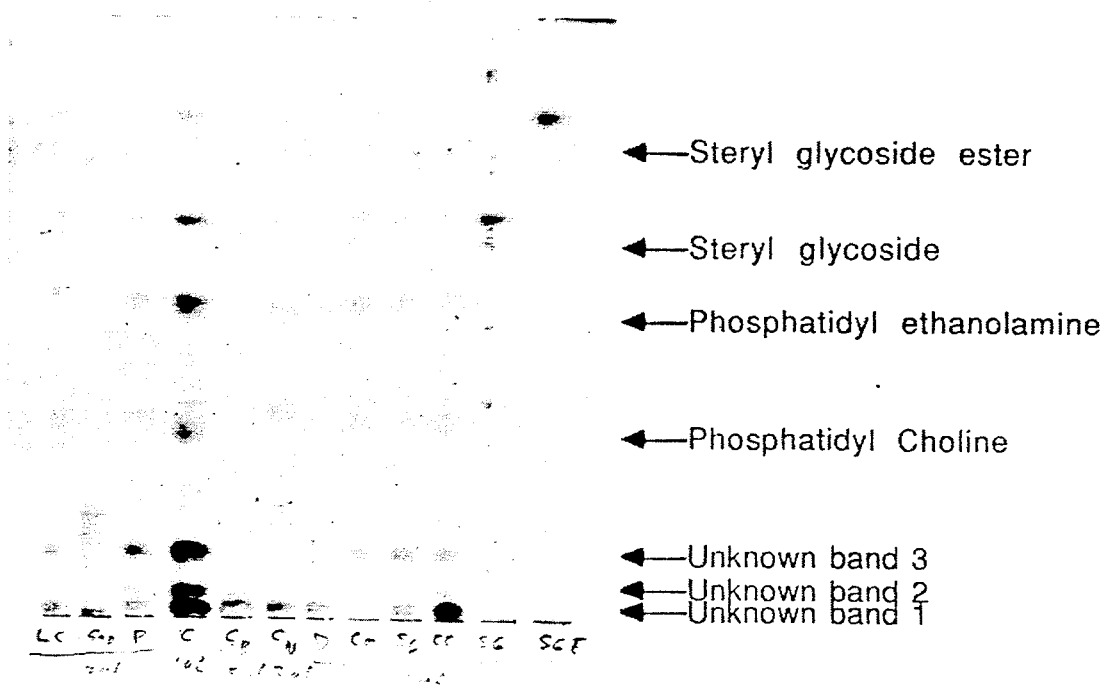
FIG. 1 is a thin-layer chromatography plate of lecithin derived phospholipid stained with orcinol spray for sugar detection.

Phospholipids or phosphatides are lipoidal compounds containing phosphorous. They are essential components of all plant and animal cells. The category of phospholipids includes lecithin. Lecithins are believed to be the only phospholipids having pharmaceutical applications. (See, Remington's Pharmaceutical Science, 17th Edition, Mack Publishing Co., Easton, PA (1985)).

A molecule of a lecithin, upon complete hydrolysis, yields two molecules of fatty acid and one molecule each of glycerol, phosphoric acid, and a basic nitrogenous compound. Typical resultant fatty acids are linoleic acid, oleic acid, palmitic acid, and stearic acid. The phosphoric acid is found in either an α- or a β-position in the glycerol, forming an α-glycerophosphoric acid or a β-glycerophosphoric acid, respectively. These correspondingly form α- and β-lecithins illustrated below, with the lecithin of each series differing in the fatty acids attached to the glycerol.

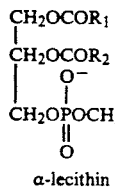

α-lecithin

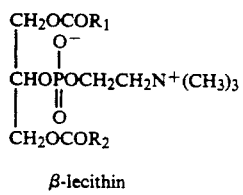

β-lecithin

Choline or its acetylated derivative, acetylcholine, typically is the basic nitrogenous compound which results from the hydrolysis of lecithin.

PROCEDURE I (Components C, D and G)

Commercially available lecithin is often obtained by extraction from lecithin sources such as egg yolk, brain tissue or soy beans. Granular soy lecithin is the lecithin preferred for use in the present invention.

The aqueous polar organic solvent solution referred to in the above procedure and useful in preparing the lecithin (or lecithin source)/aqueous polar organic solvent mixture is generally comprised of water and a water miscible hydroxycontaining compound such as a mono-, di-, or polyhydric alcohol. Preferably, the aqueous polar organic solvent solution comprises an ethyl alcohol/water solution having a weight ratio of alcohol:water of about 1:1 to about 10:1, preferably about 2:1 to about 6:1, and more preferably about 4:1.

The lecithin (or lecithin source)/aqueous polar organic solvent mixture is prepared so as to result in a solution comprised of a minor amount (i.e. less than 50 parts by weight) of lecithin, preferably about 10-40 parts by weight lecithin with the remainder being aqueous polar organic solvent, and more preferably about 20 parts by weight of lecithin and 80 parts by weight of aqueous polar organic solvent solution, based upon 100 parts by weight of lecithin and aqueous polar organic solvent solution combined.

The mixture is typically heated to about 50° C. to 120° C., preferably to about 70° to 100° C., and more preferably to about 85° C., and is held at that temperature to yield the first liquor fraction and the first insoluble fraction. Also preferably, the mixture is agitated for part of the time during which it is heated and then allowed to separate.

Additional aqueous polar organic solvent solution, as described above, is added to the first insoluble fraction in a weight ratio of additional aqueous polar organic solution:original lecithin of about 4:1 to 1:4, preferably about 2:1 to 1:2, and more preferably about 1:1. The resultant mixture is heated again as above, with or without agitation, to yield a second liquor fraction. This second liquor fraction is combined with the first liquor fraction to give a combined liquor fraction which can be allowed to cool room temperature, preferably to below 0° C., and more preferably to as low as −20° C.

After cooling, the combined liquor fraction is preferably reheated as above, again most preferably to about 85° C. Optionally, this heating and separation can be again repeated.

The resultant insoluble fractions are combined to yield a total insoluble fraction. The combined liquor fraction (or the optional total liquor fraction) is relieved of residual aqueous polar organic solvent solution, preferably with the aid of applied vacuum, yielding residual solids.

These residual solids are mixed with a polar organic solvent, preferably an anhydrous alcohol, and more preferably anhydrous ethyl alcohol, in an amount sufficient and for a period of time sufficient to leach out remaining soluble material from the residual solids, yielding remaining residual solids.

These remaining residual solids comprise Component C.

The remaining residual solids, Component C, are useful as derived, or can be further separated into a white powder composition, Component D, and a yellow crystalline composition, Component G.

Additionally, Components C, D and/or G may be diluted in an alcohol solvent, preferably a trihydric alcohol solvent, more preferably glycerin.

Component C has been found to exhibit anti-viral activity, particularly when diluted in glycerin, which is known to contain residual amounts of water. Preferably, Component C is diluted with glycerin to a composition comprising from 0.01 to 5 percent by weight of Component C, and most preferably from about 0.1 to about 1.5 percent of Component C on the same basis, with the remainder the diluent.

Component C may also be diluted in water in which it forms a stable emulsion.

Generally, viral diseases, skin manifestations thereof, and skin diseases are susceptible and responsive to treatment with Component C or dilutions thereof. These diseases include, but are not limited to: herpes, HIV, chicken pox, and influenza viruses; skin ulcers caused by herpes virus and chicken pox; some types of warts; and other less well-defined intractable ulcers, such as diabetic ulcers and the like. Pharmacological activity is also possible with respect to solid neoplasts.

Without being bound by any theory, applicants hypothesize that the presence of alkaline (positively charged) glycolipids in Component C are suited for non-specific binding with lipophilic viruses based upon both solubility and charge which, in turn, results in the observed range of anti-viral activity.

Component C can be administered topically or systemically.

A skin treating effective amount is that amount of the particular composition being utilized, or the dilution of such composition, which is administered and is sufficient to effect an improvement in the condition of a warm-blooded animal as compared to the condition for which the subject is being treated.

An anti-viral effective amount is that amount of the particular composition being utilized, or the dilution of such composition, which, when administered, is sufficient to effect an improvement in the condition of a warm-blooded animal as compared to the condition for which the subject is being treated. Alternatively, an anti-viral effective amount is that amount sufficient to result in a decrease in the activity of a virus as determined, inter alia, in a viral assay performed by methods for determining anti-viral activity which are known to those skilled in the art.

Typical dosage unit forms include ointments, suspensions, lozenges, gargles, inhalers, tablets, capsules, suppositories, and the like. Dosage unit forms may be administered topically, transdermally, orally or the like.

PROCEDURE II (Components C, D and G)

Procedure II, steps (a-i), are similar to those of Procedure I and the components, amounts and parameters are generally as described above.

However, in Procedure II, residual aqueous polar organic solvent in the third liquor fraction or the total liquor fraction is removed, preferably by vacuum, to yield residual solids. The residual solids are heated in a polar organic solvent to yield a solvent-liquor fraction. This procedure is repeated until no color is imparted to the polar organic solvent and results in remaining residual solids which are either further processed as described above or are used as obtained. Resultant Components C, D, and G are as described above, as are dosage unit forms, and methods of treatment.

PROCEDURE III

Component S-2

The total insoluble fraction is prepared with the same proportions, components, and parameters as in either Procedure I or II. Component S-2 is pro-bacterial and pro-biotic.

Procedure IV (Component 6)

The starting lecithin or lecithin source for the preparation of Component 6 are those as described above. The polar organic solvent useful in Procedure IV is preferably an anhydrous alcohol, and more preferably anhydrous ethyl alcohol. The weight ratio of lecithin (or lecithin source)/polar organic solvent in the mixture is about 1:4 to about 4:1, preferably is about 1:2 to about 2:1, more preferably is about 1:1, and most preferably is about 3:4. The mixture is typically cured at or about room temperature with gentle agitation for at least about 24 hours, preferably longer, and more preferably about four (4) days.

All cooling steps in Procedure IV are generally carried out at below room temperature (20°-25° C.), preferably below about 0° C., and more preferably below about −20° C. The reduction of polar organic solvent in the supernatant fraction generally results in a volume reduction or loss of from about 10 percent to about 50 percent, preferably from about 15 to about 20 percent, of the starting volume.

The final reduction of polar organic solvent in the upper fraction is typically conducted by vacuum distillation and concentrates the weight of the phospholipids in the fraction to from about 20 percent to about 60 percent, and preferably to about 40 percent, by weight, of the entire fraction.

Most bacteria are susceptible and responsive to treatment with Component 6, including but not limited to those of the genuses Streptococcus, Staphylococcus and Proteus, as well as E. coli. An anti-bacterial effective amount is that amount of the particular composition being utilized which is sufficient to effect an improvement in the condition of a warm-blooded animal as compared to the untreated condition for which the subject is being treated. Alternatively, an anti-bacterial effective amount is the amount sufficient to suppress or decrease the growth of bacteria in a bacterial assay performed by methods known to those skilled in the art. Dilutions of Component 6 are as described above.

Methods of administration of Component 6 are as described above.

Dosage unit forms of Component 6 are as described above.

Procedure V (Component S-6)

Parameters, components, and amounts for the preparation and the derivation of the liquor fraction and the solid fraction in the Procedure V are the same as in Procedure I described above.

However, for Procedure V, the subsequent removal of aqueous polar organic solvent solution from the liquor fraction is not performed completely. Removal is stopped when a semi-solid gel state is achieved. This generally occurs when about 10 percent of the soluable fraction is still in solution.

The resultant gel is mixed with a trihydric alcohol solvent, preferably glycerin, and the remaining portion of polar organic solvent solution is removed by methods known to one of ordinary skill in the art, preferably by vacuum distillation.

The concentration of Component S-6 can be further adjusted by the addition of trihydric alcohol solvent as described above to dilutions ranging from about .01 percent to about 10 percent, preferably from about 0.5 percent to about 5 percent, and more preferably about 1.0 percent of Component S-6.

Component S-6 demonstrates both anti-bacterial and anti-viral effectiveness, as described previously.

The respective amounts of Component S-6 useful in the treatment of warm-blooded animals, the types of administration, and the amounts and types of dosage units are as described above.

Procedure VI (Components SH-2, SH-6, SH-7 AND SH-8)

Parameters, components, and amounts for the preparation and derivation of the liquor fraction and the solid fraction in Procedure VI are that a temperature of about 50° C. is used and the granular lecithin is added to 80%/20% (v/v) solution of ethyl alcohol/water in an amount of 1 kg lecithin/1 liter solution.

However, for Procedure VI, the temperature is generally maintained at a substantially constant level throughout the manipulative steps, including the agitation and repeated separation step.

Components SH-6, SH-7, and SH-8 demonstrate both anti-bacterial and anti-viral effectiveness, as described previously, to varying degrees. Component SH-2 has reduced anti-viral effectiveness and is pro-bacterial.

The respective amounts of Components SH-6, SH-7, and SH-8 useful in the treatment of warm-blooded animals, the types of administration, and the amounts and types of dosage units are as described above.

Lecithin Dilutions

Commercial granular lecithin contains compounds that are therapeutically valuable against lipophilic viral infection and other less well-defined conditions such as intractable skin ulcers. This value can be exploited by taking advantage of the solubility differential of the varying constituents of granular lecithin, particularly in a trihydric alcohol solvent, and most particularly in U.S.P. glycerin which already contains a certain amount of water. Other solvents suitable for dilution of lecithin include polyethylene glycol, such as polyethylene glycol having a molecular weight of about 400-600. Water may also be used as a diluent.

Surprisingly, the pharmacological and anti-viral effects of granular lecithin are increased as the concentration of lecithin in the lecithin/solvent combination decreases, particularly when the concentration of lecithin ranges from about 0.5 to about 10 parts by weight and the solvent ranges from about 99.5 to about 90 parts by weight. Preferably, the lecithin ranges from about 1 to about 5 and glycerin from about 99 to about 95 parts by weight. Both of the above ranges are based upon 100 parts by weight of lecithin and glycerin combined. Without being bound by any particular theory, it is hypothesized that at the lower concentrations, a dissociation effect occurs in which there is adequate space for components to separate from accompanying or complementary compounds. Therefore, surprisingly, lower concentrations of lecithin are generally more effective than higher concentrations.

Lecithin useful in these dilutions is as described above. The trihydric alcohol preferably comprises glycerin.

Conditions which can be treated with the lecithin dilutions include skin ulcers and pharyngitis. Furthermore, flu-like symptoms associated with pharyngitis have been treated successfully.

Dosage unit forms which are contemplated by the present invention are as described above, as are the respective amounts which are useful. Administration is as described above as well.

DESCRIPTION OF THE PREFERRED EMBODIMENTS

The following examples illustrate the invention without limitation.

In the following Examples of the Procedures of the present invention, the commercial lecithin utilized, unless indicated otherwise, was a product of Riceland Foods, Inc. designated under the trademark LECIGRAN$^{TM}$. This product is said to have the nutritional information and typical compositional analysis as set forth in TABLES A and B, respectively, below.

TABLE A

| LECIGRAN Nutritional Information | | |
|---|---|---|
| Per 100 Grams: | | |
| Calories | 700 | |
| Protien | 0 g | |
| Carbohydrate | 8 g | |
| Fat | 91 g | |
| Fatty Acids | 50 g | |
| Polyunsaturated | 33.0 g | |
| Monounsaturated | 4.5 g | |
| Saturated | 12.5 g | |
| Cholesterol | 0 g | |
| Phosphatidylcholine | 23.5 g | |
| Phosphatidylethanolamine | 20.0 g | |
| Phosphatidylinositol | 14.0 g | |
| Potassium | 1.2 g | |
| Linoleic Acid | 29.5 g | |
| Linolenic Acid | 3.5 g | |
| PERCENTAGE OF U.S. RDA (per 7.5 g serving): | | |
| Protein* | Thiamine* | Iron 2 |
| Vitamin A* | Riboflavin* | Phosporous 25 |
| Vitamin C* | Niacin* | Magnesium 4 |
| Vitamine E* | Calcium* | |

*Contains less than 2% of the U.S. RDA of these neutrients.

TABLE B

| LECIGRAN Compositional Information | |
|---|---|
| TYPICAL COMPOSITION: | |
| Acetone Insolubles | 97% |
| Phosphatidylcholine | 26% |
| Choline | 3.6% |
| Phosphatidylethanolamine | 20.0% |
| Inositol Phosphatides | 14.0% |
| Inositol | 2.2% |
| Phosphatidylserine | 4.0% |
| Phytoglycolipds | 13.0% |
| Other phosphatides, lipids | 14.5% |
| Carbohydrates | 8.0% |
| Sucrose | 3.2% |
| Raffinose | 0.8% |
| Stachyose | 4.0% |
| Soybean Oil | 2% |
| Moisture | 1% |
| TYPICAL ANALYSIS: | |
| Relative Fatty Acid Composition | |
| Palmitic | 20% |
| Stearic | 5% |
| Oleic | 9% |
| Linoleic | 59% |
| Linolenic | 7% |
| Phosphorus | 3.0% |
| Nitrogen | 2.0% |
| Potassium | 1.2% |
| Calcium | 0.07% |
| Magnesium | 0.10% |
| Sodium | 0.03% |
| Soya Tocopherols | 500 ppm |
| Sterols | 1,000 ppm |
| Cholesterol | 0 mg/100 g |
| Protein | 0.0% |
| Calories | 7.0/g |
| Ash | 8.5% |
| Iodine Value | 85 |
| Bulk Density | 0.42 g/cc |

EXAMPLE 1

Preparation of Component C by Method of Procedure II and Analysis

An aqueous polar organic solvent solution of 80% by volume of ethyl alcohol and 20% by volume of water was prepared, and granular lecithin ("source") was added at a concentration of 100 gms of lecithin per 400 ml of aqueous polar organic solvent solution. The resultant mixture was then heated to 85° C.

When the temperature reached 85° C., the mixture was agitated and was held at 85° C. until a first liquor fraction and a first insoluble fraction evolved. The fractions were separated, and 100 ml of the aqueous polar organic solvent solution (80% ethyl alcohol/20% water) per 100 gms of starting granular lecithin were added to the first insoluble fraction.

This resultant mixture was heated to 85° C., and resulted in a second liquor fraction and second insoluble fraction. The second liquor fraction was added to the first liquor fraction to yield a combined liquor fraction. The combined liquor fraction was reheated to 85° C., resulting in a third liquor fraction and a third insoluble fraction; this third insoluble fraction was separated and was added to the previous insoluble fraction. The third liquor fraction was relieved of solvent by means of vacuum distillation to yield residual solids.

The residual solids were then heated in a polar organic solvent, anhydrous ethyl alcohol, to 75° C., which resulted in a colored liquor portion. The colored liquor portion was separated, and the preceding step was repeated until no color was imparted to the alcohol.

The remaining insoluble component is Component C and was analyzed by thin-layer chromatography. Thin-layer chromatography was conducted on thin layers of silica using chloroform/methanol/water (60:35:8 (v/v/v)) as the mobile phase. The results are illustrated in FIGS. 1, 2 and 3.

In FIG. 1, the plate was stained with orcinol reagent which reacts with sugars to give a characteristic dark purple color. Orcinol reagent will also react with some phospholipids to produce a color that is brown rather than purple.

Figure 2:
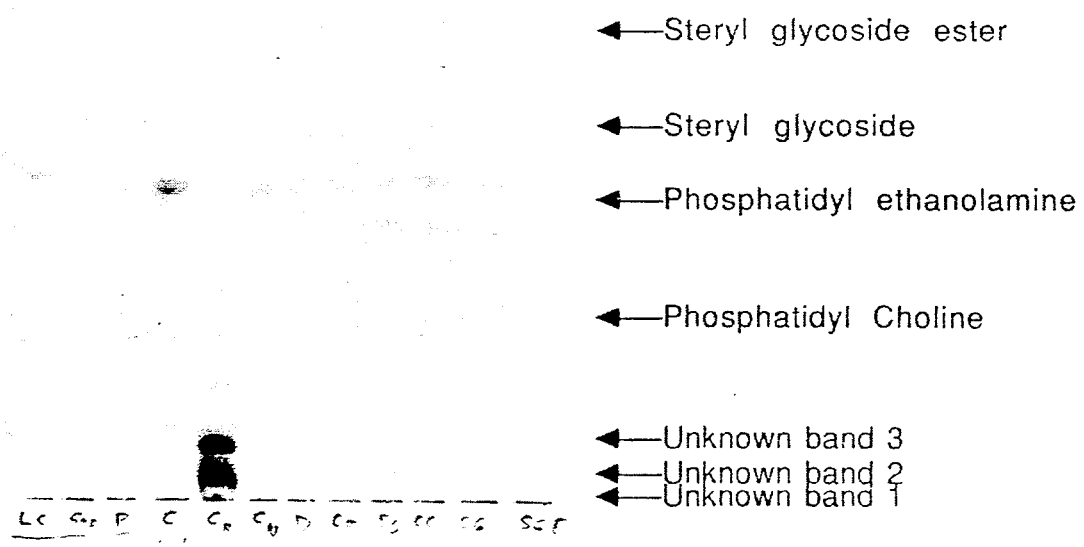
FIG. 2 is a thin-layer chromatography plate of lecithin derived phospholipid stained with ninhydrin spray for amino nitrogen detection.

In FIG. 2, the plate was stained with ninhydrin spray for amino nitrogen detection.

Figure 3:
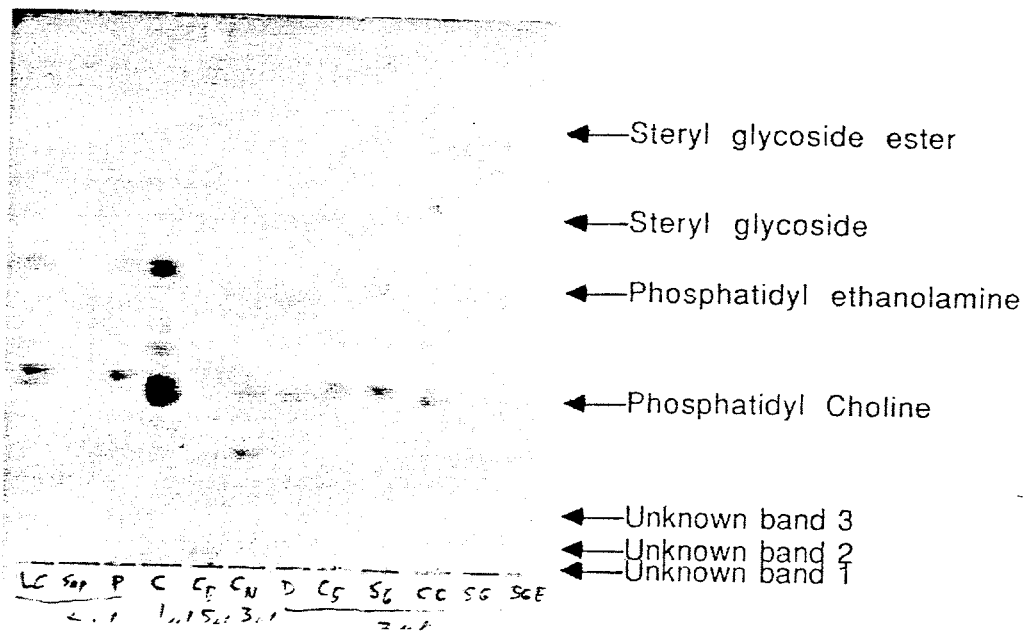
FIG. 3 is a thin-layer chromatography plate of lecithin derived phospholipid stained with Russian spray for phosphate detection.

In FIG. 3, the plate was stained with Russian spray for phosphate detection.

FIG. 1 contains an esterified steryl glucoside standard which allows identification of the least polar, major sugarcontaining constituents of the fractions, such as esterified steryl glycosides (1). The next lower major bands have the same Rf and reactivity to orcinol as steryl glucoside (3). The third major set of bands from the top should be phosphatidyl ethanolamine (5), based upon its Rf, reactivity to orcinol, and positive reaction with ninhydrin reagent, as in FIG. 2, and with Russian spray, as in FIG. 3. The fourth major set of bands from the plate appear to be phosphatidyl choline (7) based upon its chromatographic behavior, its lower reactivity with ninhydrin, as in FIG. 2 (as quaternary amines do not react well with ninhydrin), and its strong, positive reaction with Russian spray, as in FIG. 3.

Component C was also run through a cation exchange column to separate out basic materials. The lipids that were bound to this column were designated as $C_B$. Those that passed through the column without binding were designated Component $C_n$. $C_c$ represents all of the crystalline material in Component C. Component C is capable of forming a stable emulsion in water. It also forms a stable emulsion in 50% (v/v) methanol in water, but exhibits a slightly lower solubility in this medium. Component C is somewhat soluble in glycerol/ water solutions, but was not soluble in less polar solvents.

EXAMPLE 2

Preparation of Component D

Component C was prepared according to the method of Example 1, and was further separated into a white powdery substance, and a yellow crystalline substance. The white powdery substance is Component D. Component D was analyzed by thin-layer chromatography. The results are shown in FIGS. 1, 2 and 3.

EXAMPLE 3

Component D was prepared according to the method of Example 2 and was diluted with a trihydric alcohol solvent, glycerin, to a 0.1% (w/w) solution.

EXAMPLE 4

Preparation of Component G

Component C was prepared according to the method of Example 1, and a yellow crystalline solid, Component G, was separated out of the residual solids. Component G was analyzed by thin-layer chromatography. The results are shown in FIGS. 1, 2 and 3.

EXAMPLE 5

Component C was prepared according to the method of Example 1 and was diluted to concentrations of 0.1%, 1% and 1.2% (w/w), in a trihydric alcohol solvent, glycerin.

EXAMPLE 6

Anti-HIV virus effectiveness of Component C was tested in duplicate by inoculating the cell line CEM-IW with Component C prepared according to the method of Example 1 in various concentrations, as illustrated in Tables 1 and 3. Plates were incubated for seven days, and the number of remaining viable cells was determined using a colorimetric end point. The results of the duplicate tests are illustrated in Tables 1 and 2 and Tables 3 and 4, respectively.

Example 6 indicates the moderate anti-HIV virus activity of Component C.

TABLE 1

| SUMMARY | | DOSE | INFECTED RESPONSE | UNINFECTED RESPONSE |
|---|---|---|---|---|
| Index | Concentration | ($\mu$g/ml) | Percent of Control | Percent of Control |
| IC50[A] ($\mu$g/ml) | $>2.50 \times 10^{+2}$ | $7.94 \times 10^{-2}$ | 9.57 | 99.46 |
| EC50[B] ($\mu$g/ml) | | $2.51 \times 10^{-1}$ | 9.63 | 106.30 |
| TI50[C] (IC/EC) | | $7.93 \times 10^{-1}$ | 9.00 | 106.63 |
| | | $2.50 \times 10^{0}$ | 10.36 | 108.69 |
| | | $7.92 \times 10^{0}$ | 8.27 | 110.35 |
| | | $2.50 \times 10^{+1}$ | 15.81 | 109.49 |
| | | $7.91 \times 10^{+1}$ | 20.33 | 114.47 |
| | | $2.50 \times 10^{+2}$ | 36.57 | 90.09 |

[A]Concentration of drug resulting in 50% growth inhibition as derived from normal, uninfected cultures.
[B]Concentration of drug that results in a 50% reduction of cytopathic effect.
[C]In vitro therapeutic index: $\frac{IC50}{EC50}$.

TABLE 2
IN VITRO ANTI-HIV DRUG SCREENING RESULTS

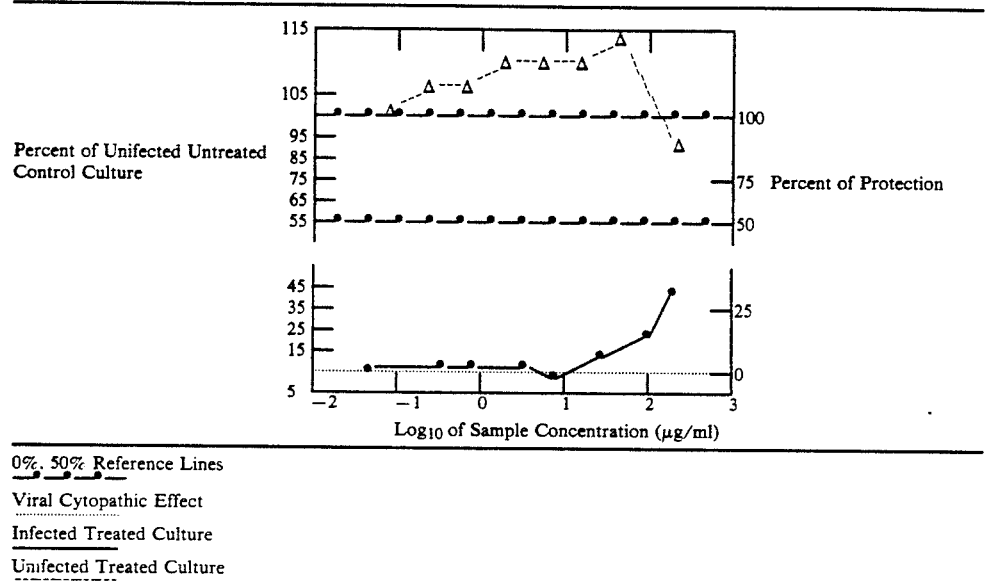

0%, 50% Reference Lines

Viral Cytopathic Effect

Infected Treated Culture

Unifected Treated Culture

TABLE 3

| SUMMARY | | DOSE | INFECTED RESPONSE Percent | UNINFECTED RESPONSE Percent |
|---|---|---|---|---|
| Index | Concentration | ($\mu$g/ml) | of Control | of Control |
| IC50[A] ($\mu$g/ml) | $>2.50 \times 10^{+2}$ | $7.94 \times 10^{-2}$ | 16.33 | 99.38 |
| EC50[B] ($\mu$g/ml) | | $2.51 \times 10^{-1}$ | 19.25 | 107.07 |
| TI50[C] (IC/EC) | | $7.93 \times 10^{-1}$ | 15.18 | 100.64 |
| | | $2.50 \times 10^{0}$ | 15.70 | 105.52 |
| | | $7.92 \times 10^{0}$ | 14.93 | 109.51 |
| | | $2.50 \times 10^{+1}$ | 16.70 | 106.92 |
| | | $7.91 \times 10^{+1}$ | 31.18 | 112.98 |
| | | $2.50 \times 10^{+2}$ | 44.33 | 111.13 |

[A]Concentration of drug resulting in 50% growth inhibition as derived from normal, uninfected cultures.
[B]Concentration of drug that results in a 50% reduction of cytopathic effect.
[C]In vitro therapeutic index: $\frac{IC50}{EC50}$.

TABLE 4
IN VITRO ANTI-HIV DRUG SCREENING RESULTS

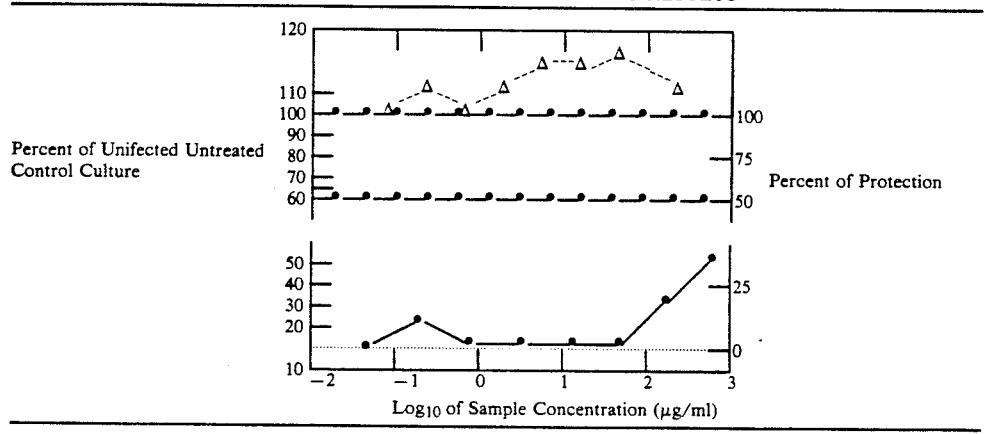

0%, 50% Reference Lines

Viral Cytopathic Effect

Infected Treated Culture

Uninfected Treated Culture

EXAMPLE 7

Component G is prepared by the method of Example 4 and is diluted with a trihydric alcohol solvent, glycerin, to a concentration of 0.1% (w/w).

EXAMPLE 8

Preparation of Component S-2 by Procedure III

An aqueous polar organic solvent solution of 80% by weight of ethyl alcohol and 20% by weight by weight of water was prepared, and granular lecithin was added at a concentration of 100 gms of lecithin per 400 ml of aqueous polar organic solvent solution. The resultant mixture was then heated to 85° C.

When the temperature reached 85° C., the mixture was agitated and was held at 85° C. until a first liquor fraction and a first insoluble fraction evolved. The fractions were separated, and an additional 100 ml of the aqueous polar organic solvent solution (80% ethyl alcohol/20% water) per 100 gms of starting granular lecithin were added to the first insoluble fraction.

This resultant mixture was heated to 85° C., and resulted in a second liquor fraction and second insoluble fraction. The second liquor fraction was added to the first liquor fraction to yield a combined liquor fraction. The combined liquor fraction was reheated to 85° C., resulting in a combined liquor portion and an insoluble portion; the insoluble portion was separated and was added to previous insoluble fration to yield Component S-2.

EXAMPLE 9

Component 2 was prepared according to the method of Example 18 and was diluted to a 41% concentration by weight in glycerin. To the sample was added 1 ml. culture broth and inoculated with a microliter of E. coli broth. A three and one-half hour incubation period was followed by plating on a culture plate. A bacteria field was observed after 24 hours.

EXAMPLE 10

A fifty-six year old male was diagnosed with a deep diabetic ulcer of the leg with necrotic base and surface oozing. Component 2 prepared according to the method of Example 18, and diluted in glycerin (Example 14), was applied topically four times a day. After one week, approximately 50% resolution of the ulcer was observed, and after three weeks, approximately 90% resolution of the ulcer was observed.

EXAMPLE 11

A sixty-four year old male was diagnosed with acne rosacea scalp lesions. Component 2 prepared according to the method of Example 18, and diluted in glycerin (Example 14), was applied topically four times a day. After two weeks, approximately 75% resolution of the scalp lesions was observed.

EXAMPLE 12

A forty-two year old female was diagnosed with an infected wound on the lower leg. Component 2 prepared according to the method of Procdure IV, and diluted in glycerin (Example 14), was applied topically four times a day. After 16 days, the wound was completely healed.

EXAMPLE 13

A 5 year old female was diagnosed with ulcerated skin on the ears. A 70% (w/w) dilution in glycerin of granular lecithin prepared according to the method of Procedure IV was applied topically with no resolution. A 5% (w/w) dilution of granular lecithin in glycerin was prepared and applied topically. After 24 hours, healing was observed with prolonged period of symptom relief; however, after 3 to 5 days reddening was observed, and the patient complained of a burning sensation. After several cycles of treatment, the symptoms end.

EXAMPLE 14

One quarter teaspoon of a 5% (w/w) dilution of Component 2 in a trihydric alcohol solvent, glycerin, and 6 oz. of water was combined to prepare a gargle. Gargling with the gargle at the onset of flu-like symptoms, including sore throat and congestion, produced mucus down load and cessation of symptoms.

EXAMPLES 15-17

Figure 4A:
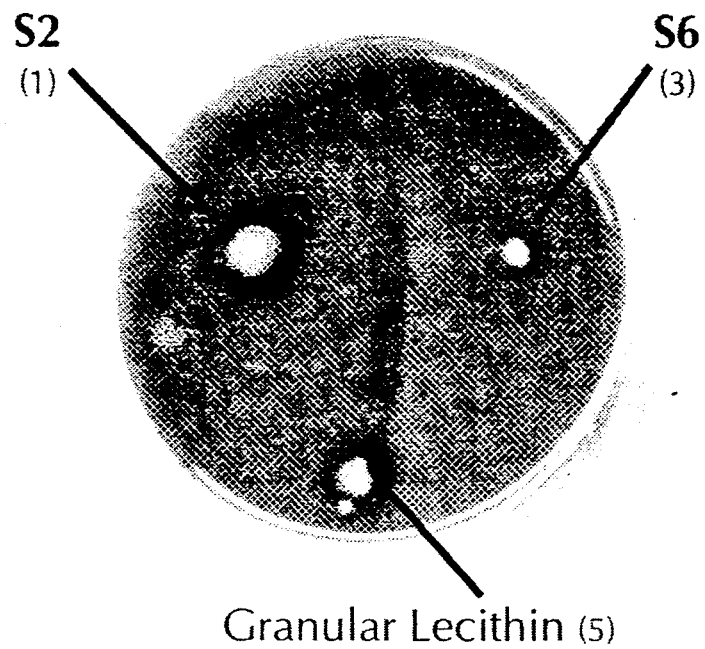
FIGS. 4a, 4b, and 4S are representations of media plates inoculated with Proteus Vulgaris containing Components S2(1), Component S-6(3) and granular lecithin (5).
Figure 4B:
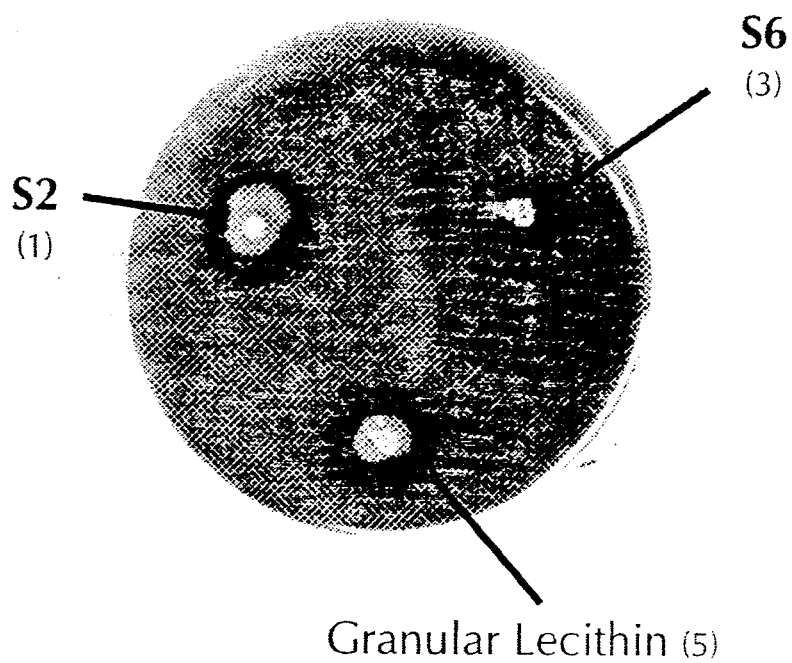
Figure 4C:
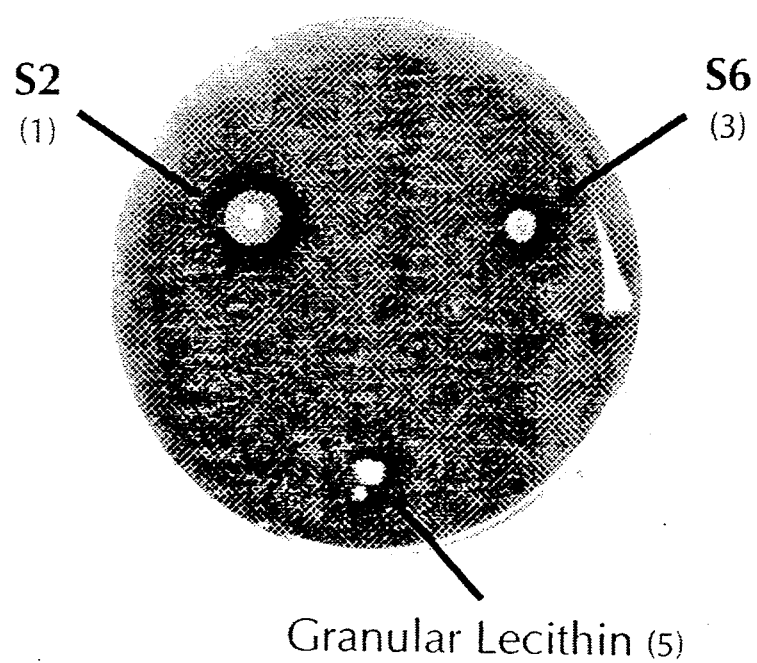
Figure 5A:
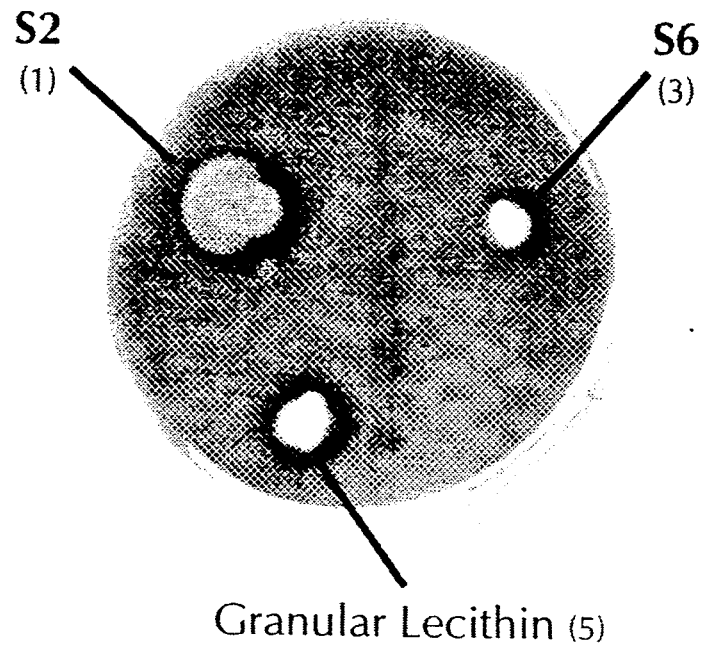
FIGS. 5a, 5b, and 5c are representations of media plates inoculated with Streptococcus containing Component S2(1), Component S-6(3) and granular lecithin (5).
Figure 5B:
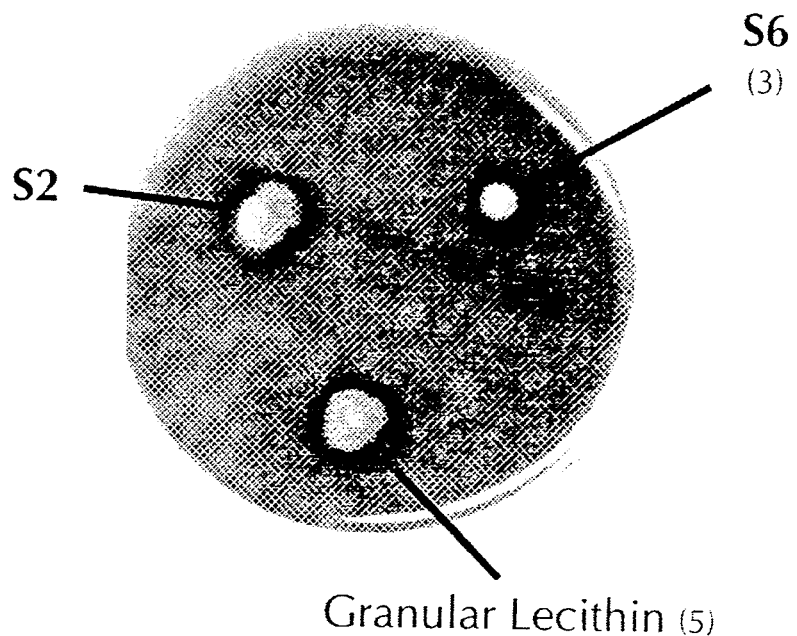
Figure 5C:
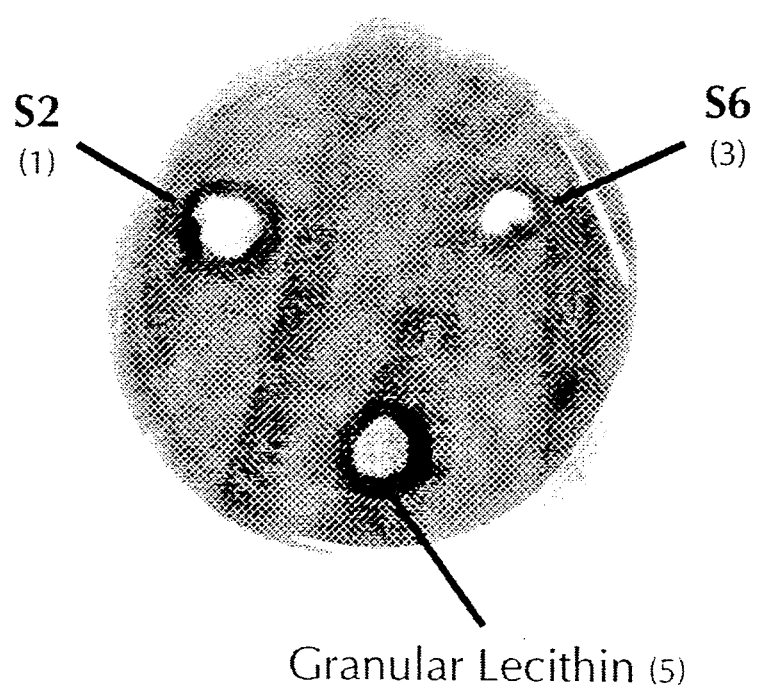
Figure 6A:
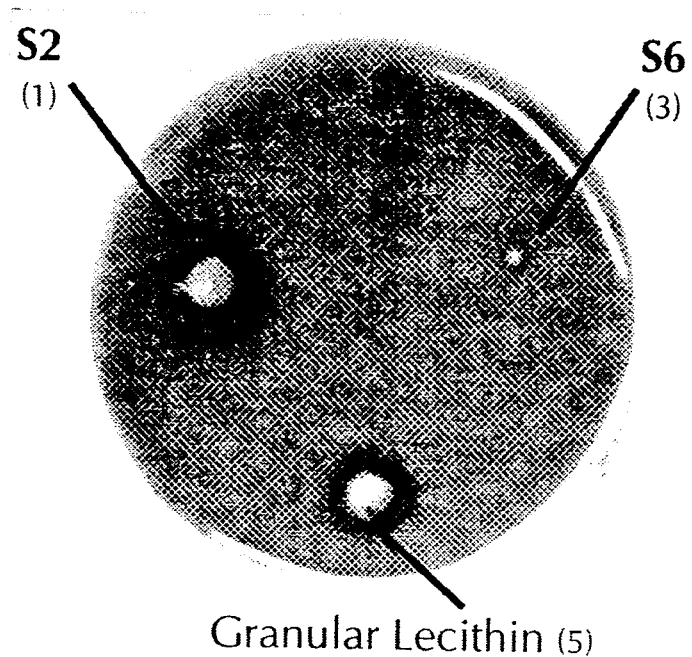
FIGS. 6a, 6b and 6c are representations of media plates inoculated with Staphylococcus Aureus containing Component S2(1), Component S-6(3) and granular lecithin (5).
Figure 6B:
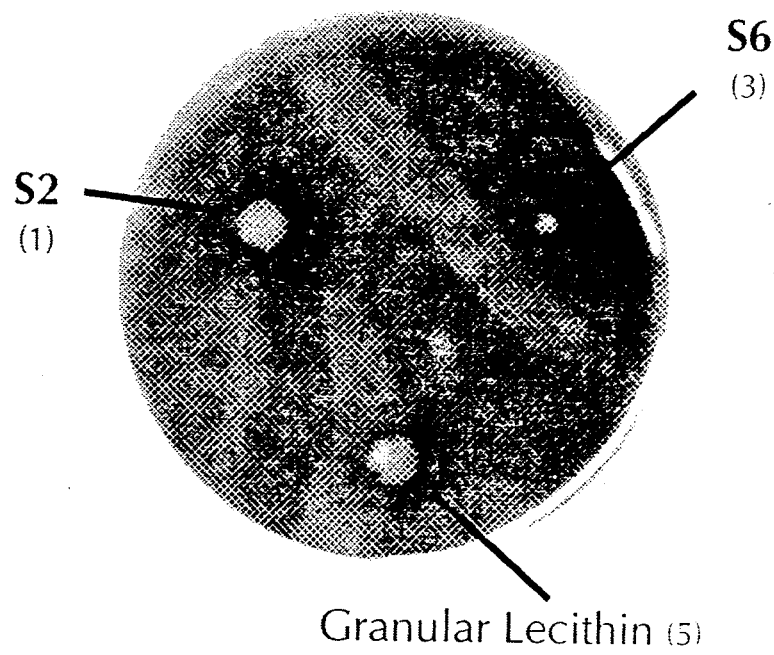
Figure 6C:
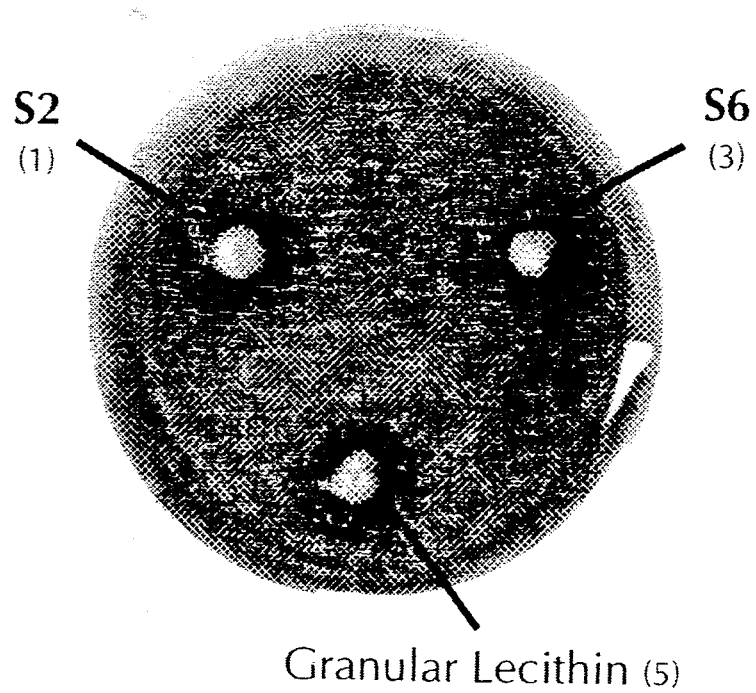

Three 24-hour broths of test bacteria Proteus vulgaris, Streptococcus bovis, and Staphylococcus aureus were individually prepared. Five drops of each broth were independently added to 500 mg. of Component S-2 prepared according to the method of Example 8. The inoculated broths were incubated at 37° C. for 24 hours. Fifteen drops of sterile water were then added to each sample. The contents were then mixed thoroughly, and 1 drop was carefully placed on culture plates using a 1 microliter inoculating loop. The plates were incubated for 24 hours at 37° C. Bacteria fields from Component S-2 inoculated broths (1) are illustrated in FIGS. 4–6.

EXAMPLE 18

Granular soy lecithin was combined with a polar organic solvent, anhydrous ethyl alcohol, at 750 gm. of lecithin per 1 liter of alcohol. The resultant mixture was left to cure for four (4) days at room temperature, with agitation, to yield a liquor fraction and a solid fraction. After this period, the liquor fraction was separated from the solid fraction. This solid fraction is Component 2. The liquor fraction was then held at −20° C. until all portions that were insoluble at this temperature were solidified leaving a supernatant polar organic solvent-based liquor portion which was then separated from the insoluble fraction while at −20° C. An amount of the alcohol equal to approximately 80-85% of the supernatant portion's total volume was then removed by means of vacuum distillation. The remaining solution was then held at −20° C. until it separated into three fractions: a lower solid fraction, an intermediate liquor fraction, and an upper liquor fraction. The upper liquor fraction was about 25% by weight of Component 6. The remaining alcohol was removed by vacuum.

EXAMPLE 19

To 500mg of Component 6 (Example 18), 5 drops each of cultured broth of E. coli. S. Aureus, S. Bovis and P. Vulgaris was added and incubated for 24 hours at 37° C. The contents were mixed and one microliter of each mixture was transferred to a culture plate. No growth was seen after 48 hours.

EXAMPLE 20

Component 6 was diluted to a 36% Component 6 by weight concentration in glycerin. One ml. of culture broth and one microliter of E. Coli culture broth was added. After incubation for 3 1/2 hours, a microliter was plated on a culture plate. No growth was recorded after 72 hours.

EXAMPLE 21

Component C was prepared according to the method of Example 1 and was diluted to a 0.15% Component C by weight concentration in glycerin for topical use.

EXAMPLES 22-23

Component C was prepared according to the method of Example 1 and was diluted in a trihydric alcohol solvent, glycerin, to a 0.1% Component C by weight (Example 22) and a 1.2% Component S-6 (by way of Example 31) by weight concentration (Example 23).

EXAMPLE 24

A Component C dilution was prepared according to the method of Example 22.

Herpes Simplex virus was grown and assayed in Vero cell culture. The titer of the virus was $2.5 \times 10^7$ tissue culture doses per 0.1 ml as indicated by the cytopathic effect of the virus after five days of incubation at 37° C.

One ml of the virus was added to 9 ml of the Component C dilution. After 10 minutes of contact at room temperature, 1:10 serial dilutions were prepared in tissue culture media. Viral controls were provided by using tissue culture media in place of the Component C dilution. Inactivation was determined by comparing the titer of the treated virus with that of the untreated virus. The presence of the virus was determined by inoculating 0.1 ml of the test preparations into each of the six cell culture flasks. The cultures were then incubated for five days and were observed for cytopathic effect.

Results are illustrated in Table 5. As can be seen from the results set forth in Table 5, Component C has an anti-viral effect on Herpes Simplex.

TABLE 5

VIRUCIDAL EFFICACY TEST (Component C)

| | Cell Line: Vero | Virus: Herpes Simplex Type I | | |
|---|---|---|---|---|
| Dilution | Virus-Control | Virus-Product | Product-Control | Cell Control |
| $10^{-1}$ | + + + + | + + + + | + + + + | − − − − |
| $10^{-2}$ | + + + + | + + + + | − − − − | − − − − |
| $10^{-3}$ | + + + + | + + + + | − − − − | − − − − |
| $10^{-4}$ | + + + + | + + + + | − − − − | − − − − |
| $10^{-5}$ | + + + + | + + + + | − − − − | − − − − |
| $10^{-6}$ | + + + + | + + − − | − − − − | − − − − |
| $10^{-7}$ | + + − − | − − − − | − − − − | − − − − |
| $10^{-8}$ | − − − − | − − − − | − − − − | − − − − |
| $10^{-9}$ | − − − − | − − − − | − − − − | − − − − |
| $10^{-10}$ | − − − − | − − − − | − − − − | − − − − |

+ = cytopathic/cytotoxic effect observed
− = no cytopathic/cytotoxic effect observed

EXAMPLE 25

A seven year old female was diagnosed with atopic eczema. Component C prepared according to the method of Example 22 was applied topically six times a day. After four days, approximately 60% resolution of the skin lesions was observed.

EXAMPLE 26

A nine year old female was diagnosed with epidermolysis bullosa dystrophica. Component C prepared according to the method of Example 22 was applied topically three times daily. After 10 days, approximately 25% resolution of the skin lesions was observed.

EXAMPLE 27

A 63 year old male was diagnosed with chemical dermatitis over his face and torso. Component C prepared according to the method of Example 22 was applied four times daily. After one week, approximately 50% resolution of the skin lesions was observed.

EXAMPLE 28

A 48 year old male was diagnosed with a skin ulcer on a thigh. Surgical debridement and repair were planned. The patient was treated topically with a 0.1% by weight Component C in glycerin solution prepared by the method of Example 22, and there was complete resolution of the ulcer, rendering the planned surgery unnecessary.

EXAMPLE 29

A 24 year old female was diagnosed with chicken pox. The patient was treated topically with 0.1% by weight Component C in glycerin solution prepared according to the method of Example 22. The lesions began to resolve in three days, along with systemic symptoms.

EXAMPLE 30

Component C was diluted in glycerin (Example 22) and used as a gargle to resolve laryngitis. No resolution was reported.

EXAMPLE 31

Preparation of Component S-6 by Procedure V

An aqueous polar organic solvent solution of 80% by volume ethyl alcohol and 20% by volume water was heated to 80°-85° C. Granular lecithin was added to the pre-heated solution at a concentration of 400 mg per liter of solution. The mixture is agitated and held at 80-85° C. until a lower insoluble fraction and an upper liquor fraction evolve (about 2 hours). The liquor fraction was then separated from the lower fraction. The liquor fraction is cooled to room temperature and re-heated to 85° C. to yield a second liquor fraction and a second insoluble lower fraction. The fractions are separated and the second liquor fraction is freed of solvent by means of vacuum.

EXAMPLES 32-34

Component S-6 was prepared according to the method of Example 31 and was diluted with a trihydric alcohol solvent, glycerin, to: less than 1% Component S-6 by weight (Example 32); 1% Component S-6 by weight (Example 33); and 5% Component S-6 by weight (Example 34).

EXAMPLES 35-37

Three 24-hour broths of test bacteria Proteus vulgaris, Streptococcus bovis, and Staphylococcus aureus were individually prepared. Five drops of each broth were independently added to 500 mgs of Component S-6 prepared according to the method of Example 31.

The inoculated broth was incubated at 37° C. for 24 hours. 15 drops of sterile water were then added to each sample. The contents were then mixed thoroughly. One drop was carefully placed on culture plates using a 1 microliter inoculating loop. The plates were incubated for 24 hours at 37° C. Bacteria fields from S-6 inoculated broths (3) are illustrated in FIGS. 4–6.

EXAMPLE 38

A 55 year old male was diagnosed with herpes simplex, genital. He was treated topically with a 1% by weight Component S-6 in glycerin solution prepared according to the method of Example 33. Severe local burning occurred and application was discontinued.

The subject was then treated with a 0.1% Component C solution in glycerin as per Example 22. Immediately relief on an active lesion occurs, seeming to cause retraction; continued daily use of the 0.1% Compound C solution in glycerine causes an increase in frequency of lesion outbreaks accompanied by, however, diminishing severity. After two months of treatment, the symptoms cease entirely (no formation of active lesions), daily use continues.

EXAMPLE 39

A 38 year old male was diagnosed with acute pharyngitis. He gargled with 5% granular lecithin and 95% glycerin gargle preparation: teaspoon of gargle in 6 oz. water. Relief of some of the symptoms (sore throat) was followed by full-blown pharyngitis in 12 hours. Supplementary to this, he gargled with 1% by weight Component S-6 in glycerin solution prepared according to the method of Example 33 - teaspoon in water, and inhaled the same Component S-6 dilution with a nebulizer. Partial relief (cough, sore throat and nasal congestion relieved) was observed after 24 hours. He was then treated with 1% by weight Component S-6 in glycerin orally, which resulted in complete relief of all symptoms and resolution of the inflammation.

EXAMPLE 40

A 63 year old female was diagnosed with herpes zoster. She was treated topically with a 1% by weight solution of Component S-6 in glycerin prepared according to the method of Example 33. The lesions resolved in 4 days, and there was about a 75% reduction in local pain.

EXAMPLE 41

A 19 year old male was diagnosed with acute pharyngitis without purulent exudate. He gargled five times a day with Component S-6 prepared according to the method of Example 33 and complete healing was seen in 3 days.

EXAMPLE 42

A 6 year old male was diagnosed with acute tonsillitis and pharyngitis. He gargled with Component S-6 prepared according to the method of Example 33, followed by swallowing of the gargle. Complete resolution, without antibiotic, was observed in 3 days.

EXAMPLE 43

An 85 year old female was diagnosed with ischemic skin ulcer on her leg. She was treated with a 1% by weight solution of Component S-6 in glycerin solution prepared according to the method of Example 33. Local itching with reduction in the size of the ulcer was observed.

EXAMPLE 44

A 94 year old female was diagnosed with an upper respiratory infection with pulmonary congestion and cough. She was unable to ambulate. She gargled with, and inhaled with a nebulizer, a 1% Component S-6 by weight dilution of in glycerin solution prepared according to the method of Example 33. Clinical improvement in symptoms was seen in 24 hours, and she was able ambulate in 48 hours.

EXAMPLE 45

A Component S-6 dilution was prepared according to the method of Example 33. Herpes Simplex virus was grown and assayed in Vero cell culture. The titer of the virus was $2.5 \times 10^7$ tissue culture doses per 0.1 ml as indicated by the cytopathic effect of the virus after four days of incubation at 37° C.

One ml of the virus was added to 9 ml of Component S-6 dilution. After 10 minutes of contact at room temperature, 1:10 serial dilutions were prepared in tissue culture media. Viral controls were provided by using tissue culture media in place of the Component S-6 dilutions. Inactivation was determined by comparing the titer of the treated virus with that of the untreated virus. The presence of the virus was determined by inoculating 0.1 ml of the test preparations into the monolayer. The cultures were then incubated for 4 days and observed for cytopathic effect. Results are illustrated in Table 6.

Aliquots of supernatant were removed from each well and were added to a freshly prepared monolayer of Vero cells. The presence of any virus particles was confirmed by cytopathic effect observed after four days of incubation.

TABLE 6

| | VIRUCIDAL EFFICACY TEST (Component S-6) | | | |
|---|---|---|---|---|
| | Cell Line: Vero | Virus: Herpes Simplex Type I | | |
| Dilution | Virus-Control | Virus-Product | Product-Control | Cell Control |
| $10^{-1}$ | + + + + | + + + + | + + + + | – – – – |
| $10^{-2}$ | + + + + | + + + + | – – – – | – – – – |
| $10^{-3}$ | + + + + | + + + + | – – – – | – – – – |
| $10^{-4}$ | + + + + | + + + + | – – – – | – – – – |
| $10^{-5}$ | + + + + | + + + + | – – – – | – – – – |
| $10^{-6}$ | + + + + | – – – – | – – – – | – – – – |
| $10^{-7}$ | + + – – | – – – – | – – – – | – – – – |
| $10^{-8}$ | – – – – | – – – – | – – – – | – – – – |
| $10^{-9}$ | – – – – | – – – – | – – – – | – – – – |
| $10^{-10}$ | – – – – | – – – – | – – – – | – – – – |

+ = cytopathic/cytotoxic effect observed
– = no cytopathic/cytotoxic effect observed

EXAMPLE 46

Preparation of Component SH-2, SH-6, SH-7, and SH-8 by Procedure VI

An aqueous solution of polar organic solvent is prepared by mixing ethyl alcohol and water in a ratio of 80:20, weight percent. Granular lecithin is added to the solution at a concentration of 1 kilogram of granular lecithin per liter of aqueous polar organic solvent solution. The resulting mixture is heated to 50° C. and held at that temperature for two hours. A yellow liquor develops above an amber lower layer. These two phases are then agitated together, while maintaining the temperature at about 50° C. The agitated mixture is left to stand to again separate, while still maintaining the temperature at about 50° C. A cloudy, opaque yellow liquor forms above a bottom layer. The cloudy, opaque yellow liquor is Component SH-6, while the bottom layer is Component SH-2. The SH-6 component is then cooled by placing in a freezer at −20° C. The portion of the solution which solidifies after 24 hours is Component SH-8. The portion which remains in solution after 24 hours is Component SH-7.

Thereafter, in another set of experiments, the sugar content of various components of the present invention was determined. It was determined that a correlation exists between anti-viral effectiveness and sugar content of the several components of the present invention; specifically, that an increase in the galactose content correlates well to the increase (relative) of anti-viral activity between the components. The percent by weight of galactose content of samples of various components disclosed herein are set forth in Table 7. More particularly, compositions comprised of one or more lecithin fractions, or comprised of one or more fractions derived from a source of lecithin, which contain residual phospholipid and have a galactose content (relative) at least equal to, and preferably greater than, and more preferably at least about 10% (relative) greater than, the galactose content of the starting lecithin or source of lecithin, have acute anti-viral activity.

TABLE 7

PERCENT GALACTOSE (RELATIVE) IN SAMPLES OF COMPONENTS

| | Lecithin | #2 | #6 | SH2 | SH6 | SH8 | S-2 | S-6 | C | D | G |
|---|---|---|---|---|---|---|---|---|---|---|---|
| Gal | 1.4 | 1.4 | 0.6 | 1.2 | 1.7 | 1.5 | 0.5 | 1.5 | 2.7 | 5.8 | 4.5 |

Anti-viral activity has been shown in dilutions of granular lecithin, Component 2, Component S-6, Component C, and Component D, while Component 6, and Component S-6, show anti-bacterial activity as well. Component S-2 and Component 2 have been shown to be pro-bacterial in nature.

The anti-bacterial suppressive features of those components evidencing anti-bacterial effectiveness can broadly be described as being those products of fractionation processes wherein the relative amount of polyunsaturates in the component is increased. Thus, a relative increase in the polyunsaturate content of a fraction or component is directly related to an increase in the ability of the fraction or component to suppress bacteria.

EXAMPLE 47

An 11 year old female was diagnosed with eczema skin behind ear. She was treated with 5% by weight granular lecithin/95% by weight glycerin solution. There was complete resolution after seven weeks of therapy.

EXAMPLE 48

A 5 year old female was diagnosed with pharyngitis with flu-like symptoms. She was treated with 5% by weight granular lecithin/95% by weight in glycerin—a ¼ teaspoon in 6 oz. of water gargle. She was afforded moderate clinical relief in 4 hours and complete relief in 24 hours.

EXAMPLES 49-51

Three 24-hour broths of test bacteria Proteus vulgaris, Streptococcus bovis and Staphylococcus aureus were prepared. Five drops of each broth were independently added to 500 mgs of granular lecithin separately. The inoculated broths were incubated at 37° C. for 24 hours. 15 drops of sterile water were then added to each sample. The contents were then mixed thoroughly, and 1 drop of the broth was carefully placed on a culture plate using a 1 microliter inoculating loop. The plates were incubated for 24 hours at 37° C. Bacterial fields from granular lecithin inoculated broths (5) are illustrated in FIGS. 4-6.

All patents, applications, publications, and test methods mentioned above are hereby incorporated by reference.

Many variations of the present invention will suggest themselves to those skilled in this art in light of the above, detailed description. All such obvious variations are within under the full intended scope of the appended claims.

We claim:

1. A method for the preparation of lecithin derived phospholipid fraction, said method comprising:
    (a) mixing lecithin or a lecithin source in a polar organic solvent to provide a mixture;
    (b) curing the mixture to yield a liquor fraction and an insoluble fraction;
    (c) cooling the liquor fraction to provide a precipitant fraction and a polar organic solvent-based supernatant liquor fraction;
    (d) reducing the amount of polar organic solvent in the supernatant liquor fraction;
    (e) cooling the reduced supernatant liquor fraction to provide three fractions comprising a lower solid fraction, an intermediate liquor fraction, and an upper liquor fraction; and optionally
    (f) reducing the amount of polar organic solvent in the upper liquor fraction.

2. A composition prepared by the method as defined in claim 1.

3. A composition comprised of the insoluable fraction from step (b) of claim 1.

4. A dosage unit form comprising an anti-viral effective amount of a composition as defined in claim 3.

* * * * *